US00PP36200P2

(12) United States Plant Patent
Head et al.

(10) Patent No.: US PP36,200 P2
(45) Date of Patent: Oct. 15, 2024

(54) ***ROSMARINUS* PLANT NAMED 'Tuscan Beauty'**

(50) Latin Name: *Rosmarinus officinalis*
Varietal Denomination: Tuscan Beauty

(71) Applicants: Stephen Head, Chilliwack (CA); Julie Head, Chilliwack (CA)

(72) Inventors: Stephen Head, Chilliwack (CA); Julie Head, Chilliwack (CA)

( * ) Notice: Subject to any disclaimer, the term of this patent is extended or adjusted under 35 U.S.C. 154(b) by 0 days.

(21) Appl. No.: 18/443,293

(22) Filed: Feb. 15, 2024

(51) Int. Cl.
*A01H 5/02* (2018.01)
*A01H 6/50* (2018.01)

(52) U.S. Cl.
USPC ..... Plt./258
CPC ..... *A01H 6/50* (2018.05)

(58) Field of Classification Search
USPC ..... Plt./258
CPC ..... A01H 5/02
See application file for complete search history.

*Primary Examiner* — Kent L Bell
(74) *Attorney, Agent, or Firm* — Weatherly IP Solutions, LLC; James M. Weatherly

(57) ABSTRACT

A new and distinct cultivar of *Rosmarinus* plant named 'Tuscan Beauty' that is characterized by dense compact plant habit, foliage which appears to be variegated arising (on closer inspection) as individual leaves that are involute in shape, or longitudinally rolled such that the lighter green abaxial surfaces are rolled or folded over the darker green adaxial surfaces. 'Tuscan Beauty' exhibits strongly aromatic foliage which is characteristic of the genus and culinary herb Rosemary and bears pale blue to mid blue bilabiate flowers from spring until late summer. Plants of 'Tuscan Beauty' reach 102 cm. in height and 90 cm. in width at maturity but may be maintained as a low-growing juvenile plant if tip-pruned in the first season of growth. 'Tuscan Beauty' is hardy to USDA Zone 7. In combination, these traits set 'Tuscan Beauty' apart from all other existing varieties of *Rosmarinus* known to the inventors.

3 Drawing Sheets

Figure 1:
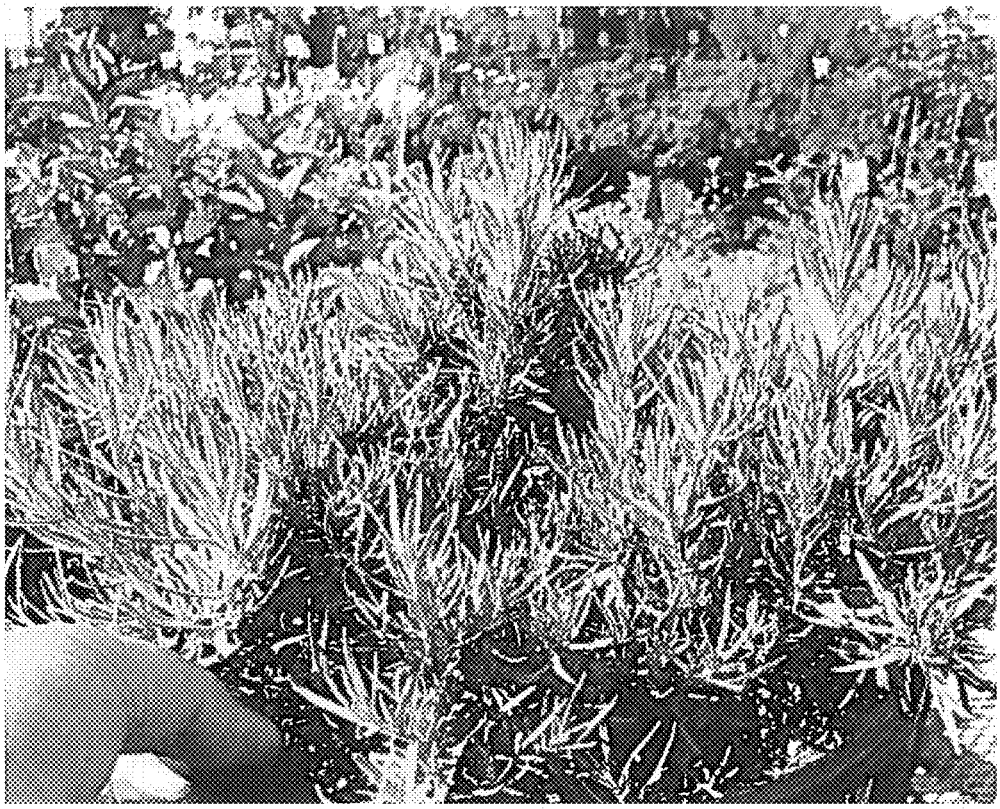

Genus and species: *Rosmarinus officinalis.*
Variety denomination: 'Tuscan Beauty'.

BACKGROUND

The present invention relates to a new and distinct cultivar of rosemary plant grown as an ornamental for use in the landscape. The new cultivar from the family Lamiaceae is known botanically as *Rosmarinus officinalis* and will be referred to hereinafter by the cultivar name 'Tuscan Beauty'.

'Tuscan Beauty' was discovered, by the inventors, in 2016 as a naturally occurring branch sport of *Rosmarinus officinalis* 'Tuscan Blue' (unpatented). 'Tuscan Blue' is a long-established non-variegated variety of Mediterranean origin which is grown as an ornamental shrub or as a culinary herb. The inventors selected 'Tuscan Beauty' in Chilliwack, British Columbia, based on the criterion of unique involute foliage which presents as leaf variegation.

'Tuscan Beauty' was discovered as a branch mutation at the inventors' nursery within a commercially grown crop of 'Tuscan Blue'. The parent is an individual *Rosmarinus officinalis* 'Tuscan Blue'.

The first asexual propagation of 'Tuscan Beauty' was conducted by the inventors in 2018 and took place at the inventors' nursery in Chilliwack, British Columbia, Canada. The method of asexual propagation used was vegetative stem cuttings rooted under mist with bottom heat. Since that time under careful observation, 'Tuscan Beauty' has remained stable, and reproduces true to type in subsequent generations of asexual propagation.

COMPARISON OF 'TUSCAN BEAUTY' WITH ITS SPORT PARENT VARIETY

The new *Rosmarinus* cultivar named 'Tuscan Beauty' is distinguishable from the parent by thick involute (longitudinally rolled) leaves which appear to be variegated as the lighter abaxial surface rolls or folds over the darker adaxial surface.

COMPARISON OF TUSCAN BEAUTY WITH CLOSEST KNOWN CULTIVARS

The closest comparison plant known to the inventors is *Rosmarinus* 'Golden Rain' (unpatented). The comparison plant exhibits lime green foliage with narrow green banding that fades during summer months. 'Golden Rain' is slow to root and exhibits low vigor. 'Tuscan Beauty' is distinguishable from the comparison plant by robust growth, strong stems, and involute foliage which appears to be variegated as the lighter abaxial leaf surface rolls or folds over the darker adaxial leaf surface.

In addition, 'Tuscan Beauty' may be compared with the inventors' variety *Rosmarinus* 'Gold Dust' (U.S. Plant Pat. No. 19,949). Whereas the foliage of 'Gold Dust' is distinctly variegated bearing leaves which have dark green centers and broad gold margins, the foliage of 'Tuscan Beauty' appears to be variegated as a result of the involute light green lower surface rolling over the darker green upper surface. In addition, the flowers of 'Gold Dust' are darker blue (violet-blue) in color and the buds of 'Gold Dust' are purple in color. The flowers and buds of 'Tuscan Beauty' are both lighter mid-blue in color.

Plants of 'Tuscan Beauty' are soft and juvenile in their first season of growth and if the growing tips are pruned. Unpruned plants of 'Tuscan Beauty' grow rapidly with an upright plant habit, thick involute longitudinally rolled leaves with dark-green adaxial surface centers and light green abaxial rolled-over growth. During the second season of growth, pale-blue to mid-blue flowers appear at each node.

Plants of 'Tuscan Beauty' are drought-tolerant; plant vigor is greatest when grown in full sun, in well-draining soil with steady minimal to moderate water.

SUMMARY

The following traits have been repeatedly observed and represent the distinguishing characteristics of the new *Rosmarinus officinalis* cultivar named 'Tuscan Beauty'. These traits in combination distinguish 'Tuscan Beauty' from all other varieties of *Rosmarinus* known to the inventors. 'Tuscan Beauty' has not been tested under all possible conditions. Phenotypic differences may be observed with variations in environmental, climatic, and cultural conditions without however any variance in genotype.

1. 'Tuscan Beauty' exhibits dense compact plant habit.
2. The foliage of 'Tuscan Beauty' appears to be variegated. On closer inspection, the leaves are involute or longitudinally rolled such that the lighter green abaxial surfaces are rolled or folded over the darker green adaxial surfaces.
3. 'Tuscan Beauty' exhibits strongly aromatic foliage which is characteristic of the genus and culinary herb Rosemary.
4. 'Tuscan Beauty' bears pale blue to mid blue bilabiate flowers from spring until late summer.
6. 'Tuscan Beauty' reaches 102 cm. in height and 90 cm. in width at maturity but may be maintained as a low-growing juvenile plant if tip-pruned in its first season of growth.
7. 'Tuscan Beauty' is hardy to USDA Zone 7.

DESCRIPTION OF THE PHOTOGRAPHS

The accompanying color drawings illustrate the overall appearance of the new *Rosmarinus* cultivar named 'Tuscan Beauty' showing colors as true as it is reasonably possible to obtain in color reproductions of this type. Color in the drawings may differ from color values cited in the detailed botanical description, which accurately describe the actual color of the new variety 'Tuscan Beauty'. Plants depicted in the drawings are 12-months-old and growing in 1-liter containers grown out-of-doors taken in June 2023 in Santa Barbara, California.

The drawing labeled FIG. 1 depicts an entire plant of 'Tuscan Beauty' from a side perspective. The illustrated plant is in its first season of growth and has been pruned to maintain a low-growing plant habit.

Figure 2:
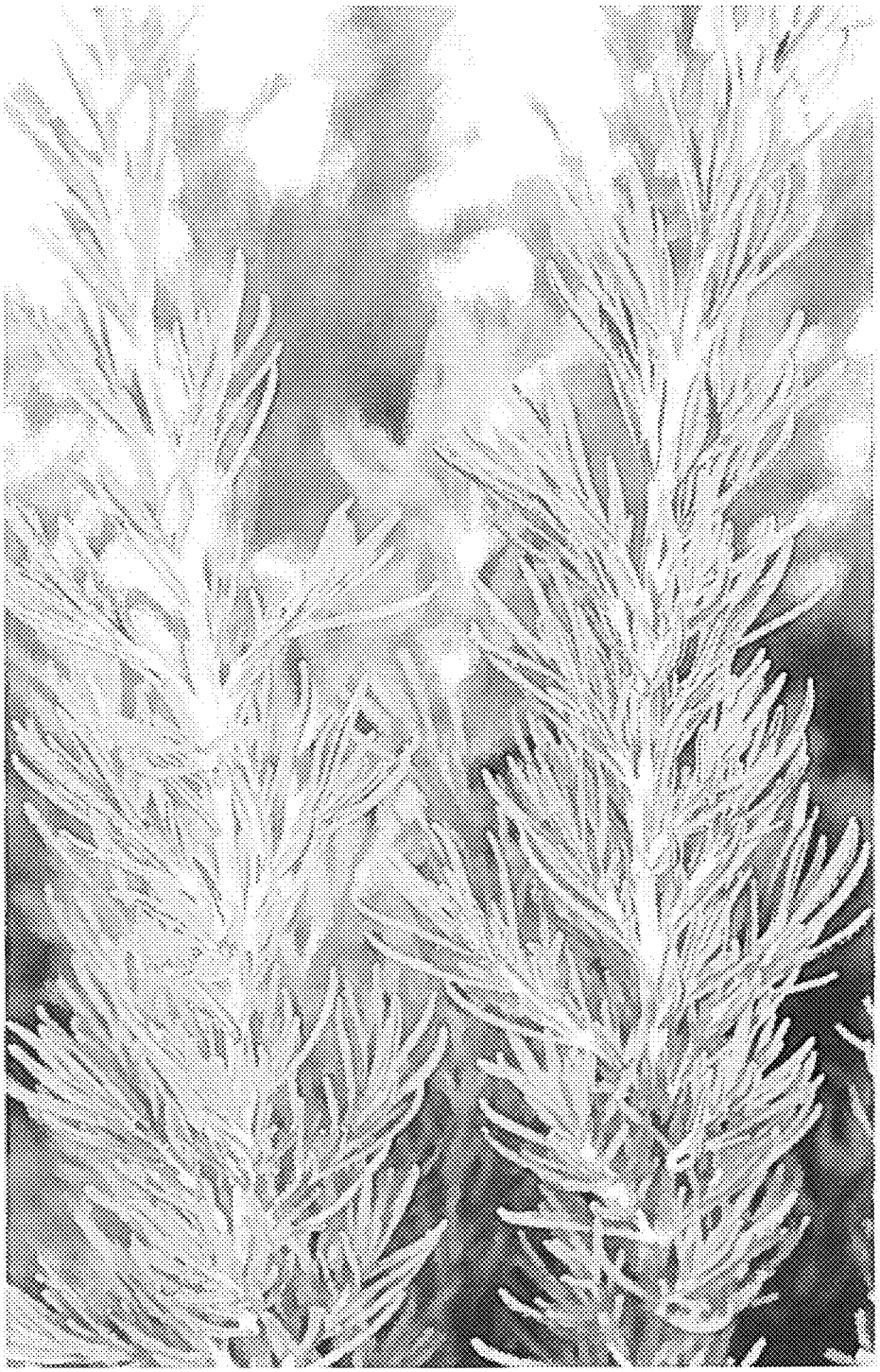

The drawing labeled FIG. 2 depicts a close-up view of foliage highlighting the distinctive involute rolled variegated foliage in which the lighter green abaxial surface is rolled or folded over the darker green adaxial surface.

Figure 3:
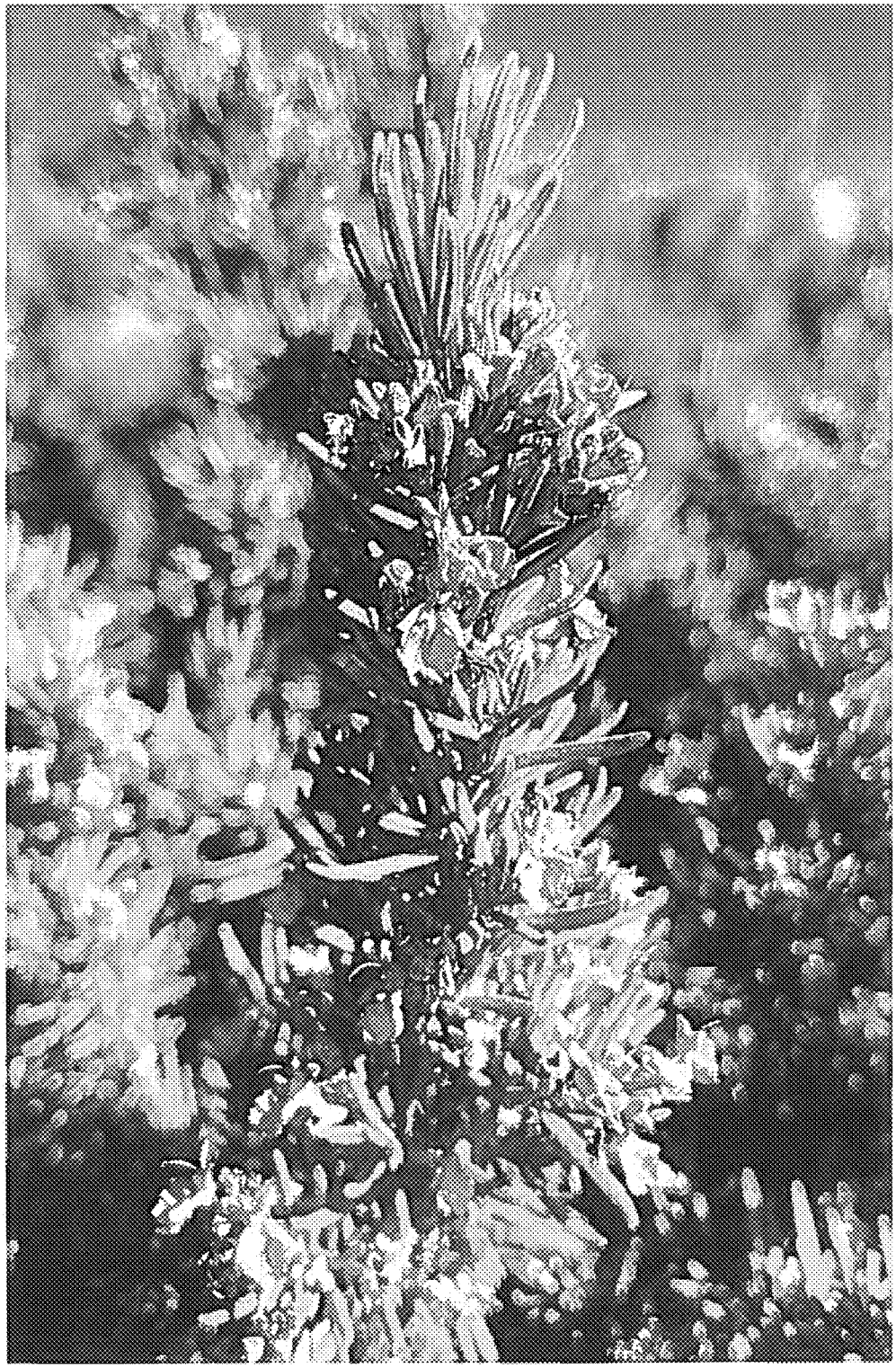

The drawing labeled FIG. 3 depicts the flowers which appear during the second season of growth.

The drawings were made using conventional techniques and although flower and foliage color may appear different from the actual color due to light reflectance, they are as accurate as possible by conventional photography.

DESCRIPTION OF THE NEW VARIETY

The following is a detailed botanical description of the new *Rosmarinus* cultivar named 'Tuscan Beauty'. Observations, measurements, values and comparisons were collected in August 2023 in Santa Barbara, California from 12-18 months old plants growing in 1-liter containers out-of-doors. Color determinations are made in accordance with The Royal Horticultural Society Colour Chart of 2007 from London England, except where general color terms of ordinary dictionary significance are used. The growing requirements of the new variety are growing in full sun, in well-draining soil with steady minimal to moderate water.

Classification:

*Botanical classification.*—*Rosmarinus officinalis* 'Tuscan Beauty'.
*Family.*—Lamiaceae.
*Genus.*—*Rosmarinus.*
*Species.*—*officinalis.*
*Denomination.*—'Tuscan Beauty'.
*Common name.*—Rosemary.

Parentage: *Rosmarinus officinalis* 'Tuscan Beauty' was discovered as a naturally occurring branch sport of the following plant: Parent: An individual *Rosmarinus officinalis* 'Tuscan Blue' (unpatented).

Plant:

*Propagation method.*—Vegetative stem cuttings.
*Rooting habit.*—Fine and fibrous, RHS 177B.
*Time to develop roots* (*range*).—Approximately 30-45 days are required to develop roots from an initial tip cutting.
*Crop time.*—6 months are required to achieve a finished 1-liter container from a rooted cutting. 18 months are required to produce a finished container plant in flower.
*Plant habit.*—Dense upright habit.
*Commercial classification.*—Shrub.
*Use.*—Ornamental for the landscape or as a container-grown culinary herb.
*Vigor.*—Low to moderate.
*Plant dimensions* (*first year, juvenile, pruned*).—10 cm. in height and 15 cm. in diameter.
*Plant dimensions* (*mature, unpruned*).—102 cm. in height and 90 cm. in width.
*Hardiness.*—USDA Zone 7.
*Cultural requirements.*—Full sun, low to moderate water, and well-draining soil.
*Pests and disease.*—As typical of the genus, 'Tuscan Beauty' is not susceptible to any pests and diseases other than general horticultural pests and diseases.

Stems and branches:

*Basal Stem* (*below first stop or pruning after establishment on own roots*).—Basal stem dimensions: Typically 3 cm in height if stopped at that point. Basal stem shape: Terete. Basal stem color: N200C. Basal stem texture: Lignified, slightly rough, glossy.
*Primary branches* (*arising from point of pruning or stimulated basally*).—Primary branch quantity: Approximately 3-5 basal branches and 5-8 branches on basal stems. Primary branch dimensions: Up to 10 cm in length and 4 mm in diameter. Primary branch stem texture: Slightly rough, glossy.

*Secondary branches* (*arising on primary branches at internodal distances of* 8 *mm.*).—Secondary branch stem quantity: Ranging between 80 and 100 branches on each primary branch. Branch stem arrangement: In opposite pairs at each node. Branch stem shape: Sub-cylindrical. Branch stem diameter: 4 mm. Branch stem length (average): 20 cm. Branch stem texture: Farinaceous.

Foliage:

*Type*.—Evergreen.
*Leaf arrangement*.—Whorled.
*Leaf division*.—Simple.
*Leaf shape*.—Linear, involute (longitudinally rolled or incurved with abaxial surface rolled or folded over adaxial surface).
*Leaf texture*.—Resinous.
*Leaf length* (*average*).—3 cm.
*Leaf width* (*average*).—0.30 cm.
*Leaf apex*.—Acute.
*Leaf base*.—Attenuate.
*Leaf quantity* (*average*).—175 leaves per secondary branch.
*Leaf color* (*adaxial surface*).—141B.
*Leaf color* (*abaxial surface*).—Ranges between 150B and 150C.
*Leaf venation pattern*.—Reticulate.
*Vein color* (*adaxial surface*).—147A.
*Vein color* (*abaxial surface*).—Inconspicuous.
*Leaf margin*.—Entire and revolute.
*Leaf surface* (*adaxial*).—Coriaceous.
*Leaf surface* (*abaxial*).—Tomentose.
*Leaf attachment*.—Sessile.
*Leaf fragrance*.—Strongly aromatic, characteristic of the herb Rosemary.

Flower:

*Inflorescence type*.—Axillary cyme.
*Flower shape*.—Bilabiate.
*Flower color*.—Initially 101B becoming 101C.
*Bud dimensions*.—3 mm. in length and 2.50 mm. in width.
*Bud apex*.—Obtuse.
*Bud shape*.—Ovoid.
*Bud color*.—101B.
*Bud surface*.—Tomentose.
*Corolla depth*.—1.25 cm.
*Corolla diameter*.—1.75 cm.
*Corolla tube depth*.—3 mm.
*Corolla*.—2-lipped and strongly exserted.
*Upper lip*.—2-lobed.
*Upper lobe apices* (*range*).—Rounded to obovate.
*Upper lip shape*.—Concave.
*Upper lip margin*.—Entire.
*Lower lip*.—3-lobed.
*Lower lobe apices*.—Rounded.
*Middle lobe shape*.—Spoon-shaped.
*Lower lip margin*.—Entire.
*Upper and lower lip dimensions* (*range*).—4-6 mm. in length and 3-8 mm. in width.
*Upper and lower lip color* (*adaxial and abaxial surfaces*).—93A.
*Upper and lower lip surfaces* (*adaxial and abaxial surfaces*).—Glabrous.
*Lips fused or unfused*.—Lips are basally fused.
*Flowering season*.—Spring until late summer.
*Aspect*.—Facing outward and upward.
*Flower quantity* (*average*).—9 per inflorescence.
*Peduncle dimensions*.—3 mm. in length and 1 mm. in width.
*Peduncle shape*.—Sub-cylindrical.
*Peduncle surface*.—Lanate.
*Peduncle color*.—147C.
*Calyx shape*.—Campanulate.
*Calyx color*.—N187B.
*Calyx surface*.—Tomentose.
*Calyx dimensions*.—5 mm. in height and 3 mm. in width.
*Number of sepals*.—3 in number.
*Fused or unfused*.—Fused.
*Sepal apex*.—Broadly acute.
*Sepal margins*.—Entire.
*Sepal color* (*adaxial and abaxial surfaces*).—N187B.
*Flower fragrance*.—None observed.

Reproductive organs:

*Stamens*.—2 parallel and strongly exserted.
*Stamen Length*.—1 cm.
*Stamen color*.—98D.
*Anther dimensions*.—1.50 mm. in length and 1.50 mm. in width.
*Anther shape*.—Disc-shaped.
*Anther color*.—156D.
*Pollen*.—None observed.
*Pistil*.—One in number.
*Pistil length*.—1 cm.
*Pistil color*.—98D.
*Stigma color*.—98D.
*Stigma length*.—1.50 mm.
*Style*.—Unbranched.
*Ovary position*.—Superior.
*Ovary shape*.—Globular.
*Ovary dimensions*.—1.50 mm. in height and 1.50 mm. in diameter.
*Ovary color*.—N144A.

Seed: No seed observed to date.

We claim:

1. A new and distinct variety of *Rosmarinus* plant named 'Tuscan Beauty' as described and illustrated herein.

* * * * *